(12) United States Patent
Funken et al.

(10) Patent No.: US 6,633,042 B1
(45) Date of Patent: Oct. 14, 2003

(54) SOLAR PHOTOREACTOR

(75) Inventors: Karl-Heinz Funken, Bonn (DE); Christian Sattler, Bonn (DE); Jurgen Ortner, Cologne (DE); Lamark de Oliveira, Cologne (DE)

(73) Assignee: DLR, Deutsches Zentrum fur Luft- und Raumfahrt e.V., Bonn (DE)

( * ) Notice: Subject to any disclaimer, the term of this patent is extended or adjusted under 35 U.S.C. 154(b) by 110 days.

(21) Appl. No.: 09/790,710

(22) Filed: Feb. 23, 2001

(30) Foreign Application Priority Data

Feb. 25, 2000 (DE) .......................... 100 09 060

(51) Int. Cl.⁷ .................. G01N 21/01; G01N 23/10; C02F 1/68; B01D 35/00
(52) U.S. Cl. ............. 250/435; 250/431; 210/764; 210/94
(58) Field of Search ............... 250/435, 431; 210/94, 764

(56) References Cited

U.S. PATENT DOCUMENTS

| | | | |
|---|---|---|---|
| 4,626,065 A | | 12/1986 | Mori |
| 4,656,141 A | * | 4/1987 | Birks et al. .............. 436/172 |
| 4,793,931 A | * | 12/1988 | Stevens et al. ........... 210/636 |
| 4,922,114 A | * | 5/1990 | Boehme ................. 250/436 |
| 5,301,203 A | * | 4/1994 | Schlie et al. .............. 372/55 |
| 5,405,368 A | * | 4/1995 | Eckhouse ................ 607/88 |
| 5,501,801 A | | 3/1996 | Zhang et al. |
| 5,620,569 A | * | 4/1997 | Scharf et al. ........... 204/157.6 |
| 5,753,106 A | * | 5/1998 | Schenck ................. 210/96.1 |
| 5,905,342 A | * | 5/1999 | Mimasu et al. ............ 315/39 |
| 6,179,972 B1 | * | 1/2001 | Kittrell ................ 204/158.2 |
| 6,468,434 B2 | * | 10/2002 | Pappa et al. .............. 210/748 |

FOREIGN PATENT DOCUMENTS

| | | |
|---|---|---|
| DE | 3710250 | 10/1988 |
| DE | 4344163 | 6/1995 |
| DE | 19714810 | 10/1998 |
| DE | 19746343 | 4/1999 |
| DE | 19844037 | 10/1999 |
| EP | 0738686 | 10/1996 |
| GB | 2118572 | 11/1983 |
| WO | WO9506111 | 3/1995 |

OTHER PUBLICATIONS

Funken, Karl–Heinz et al., "Technologies for the Solar Photochemical and Photocatalytic Manufacture of Specialities and Commodities: A Review," *Zeitschrift fur Physikalische Chemie, Bd.*, 213:99–105 (1999).

Funken, K.–H, et al., "Recent Development in Solar Photochemistry: Status and Perspectives," *Solar Thermal Concentrating Technologies*, Proceedings of the 8th International Symposium, pps 1325–1336 (1996).

(List continued on next page.)

Primary Examiner—John R. Lee
Assistant Examiner—Bernard Souw
(74) Attorney, Agent, or Firm—Hunton & Williams LLP

(57) ABSTRACT

The present invention relates to a device and method for introducing solar radiation energy into a photoreactor. This reactor can be employed for performing photochemical or photobiological reactions, i.e., syntheses, decontamination, disinfection and treatment processes. The device is characterized in that the photoreactor consists of one or more transparent outer tubes irradiated with light from the exterior, the reaction medium being passed through the tubes and thereby exposed to the radiation, wherein one or more empty transparent tubes with a smaller diameter are provided in the interior of said outer tubes, especially in a concentric arrangement, and the reaction medium is passed through the gap formed between an outer and an inner tube or, in the case of several inner tubes, through the gaps formed therebetween.

18 Claims, 4 Drawing Sheets

Degradation of TCE in water (500 mg/l), catalyst TiO₂ (200 mg/l)

OTHER PUBLICATIONS

Bahnemann, Detlef, et al., "A Self–Sufficient PV Powered Solar Detoxification Reactor for Polluted Waters," *Solar Engineering*, pps 261–267 (1997).

Braun, B., et al., "Dye–Sensitized Solar Detoxification and Disinfection of Contaminated Water," *Solar Thermal Concentrating Technologies*, Proceedings of the 8th International Symposium, pps 1391–1401 (1996).

Ajona, J.I., et al., "The Use of CPC Collectors for Detoxification of Contaminated Water: Design, Construction and Preliminary Results," *Solar Energy*, 68:109–120 (2000).

Dillert, Ralf, et al., "Field Studies of Solar Water Detoxification," Serie Ponencias, Proceedings of the 1st Users Workshop, Training and Mobility of Researchers Programme at Plataforma Solar De Almeria, pp31–40 (1997).

* cited by examiner

Degradation of TCE in water (500 mg/l),
catalyst TiO₂ (200 mg/l)

Degradation of TCE in water (500 mg/l),
catalyst TiO₂ (200 mg/l)

Degradation of OME in water (1000 mg/l)
with $TiO_2$ as a catalyst (200 mg/l)

Degradation of OME in water (1000 mg/l)
with $TiO_2$ as a catalyst (200 mg/l)

SOLAR PHOTOREACTOR

The present invention relates to a device and method for introducing solar radiation energy into a photoreactor. This reactor can be employed for performing photochemical or photobiological reactions, i.e., syntheses, decontamination, disinfection and treatment processes.

To perform photochemical or photobiological reactions, electromagnetic radiation must be provided. The economical success of a photochemical or photobiological process considerably depends on the costs of providing radiation.

The photochemical processes realized on an industrial scale and aiming at the preparation of chemicals include, for example, photohalogenations, photosulfochlorinations, photosulfoxidations, photonitrosations, photoisomerizations, photohydrodimerizations, photodesulfonations, photosulfonylations and photooxygenations. However, further reactions types not yet performed on an industrial scale are known which yield improved products with high selectivity under the action of electromagnetic radiation.

High-value added products can also be obtained from photobiological reactions. Applications for the products obtained from phototrophic cyanobacteria, algae and microalgae suggest themselves in medicine, pharmacy, beauty culture, agriculture, nutrition and in the field of environmental engineering. For example, dyes and coloring foods (e.g., phycocyanins, phycobiliproteins and carotinoids), polyunsaturated fatty acids (especially arachidonic acid, eicosapentaenic and docosahexaenic acids), antioxidants (e.g., tocopherol), proteins and polysaccharides can be prepared. Pharmacologically active substances (bactericides and fungicides) were also identified in various microalgae.

In the field of environmental engineering, photochemical and photobiological processes are developed for the detoxification and/or disinfection of water or gas streams contaminated with pollutants and/or microorganisms. It is a common feature of these processes that photonic excitation is used to form singlet oxygen, hydroxyl or other oxygen-containing free radicals, which then attack the pollutants to be degraded or microorganisms to be inactivated. Thus, the formation of excited oxygen species is possible and known by energy transfer from an electronically excited donor, by excitation of a semiconductor material, such as titanium dioxide, or by photo-Fenton's reagents.

For performing the photochemical or photobiological reactions, various radiation sources, especially light sources, are available, such as gas-discharge lamps, glow lamps, fluorescent lamps or tubes, excimer radiators and lasers. Each of these radiation sources has characteristic properties in terms of the type of the emitted spectrum and luminosity. Although lasers can provide intense radiation at a desired wavelength, the installation and operation of lasers is accompanied by such high costs that their use can be justified only in very special cases for economical reasons.

Instead of electrically operated light sources, the solar radiation may also be used for performing photochemical and photobiological reactions. Surveys of the state of solar photochemical and photocatalytic reaction engineering have already been published. The most important problems to be solved for commercialization have also been indicated therein (K.-H. Funken, D. M. Blake, M. Romero, I. Spiewak, Recent Developments in Solar Photochemistry: Status and Perspectives, in: M. Becker, M. Böhmer (eds.) Proc. 8th Int. Symp. Sol. Concentrating Technol., Oct. 6–11, 1996, Köln, Germany, C. F. Müller Verlag Heidelberg (1997), Vol. 3, 1325–1336; K.-H. Funken, J. Ortner, Technologies for the Solar Photochemical and Photocatalytic Manufacture of Specialities and Commodities: A Review, Z. Phys. Chem. 213 (1999) 99–105).

The use of voluminous open reaction vessels, or reaction vessels screened towards the environment by transparent covers, which are exposed to solar radiation has long been known. In these cases, the properties of natural sunlight are not changed, except for a weakening of the spectral radiation intensity by reflections at the surfaces of the cover and due to transmission through the cover. As a more recent development in this field, for example, DE 198 44 037 A1 describes a flat-bed solar light collector/solar reactor for solar-photochemical and solar-thermochemical syntheses. However, especially with high concentrations or with high extinction coefficients of a homogeneously dissolved chromophore or with the use of suspended heterogeneous catalyst particles or with turbid fluids, such as emulsions, the use of such voluminous reaction vessels is disadvantageous because the penetration depth of the light into the reaction mixture is very low due to light adsorption in accordance with the Lambert-Beer law and due to light scattering in the case of catalyst particles or turbid fluids.

The use of thin films is a solution to this problem, in principle. Therefore, falling film reactors have been tested for the solar detoxification of contaminated waters (D. Bahnemann, M. Meyer, U. Siemon, D. Mencke, A Self-Sufficient PV Powered Solar Detoxification Reactor for Polluted Waters, Proc. Int. Sol. Energy Conf. Solar Engineering—1997, Apr. 27–30, 1997, ASME, Washington D.C., 261–267; B. Braun, J. Ortner, K.-H. Funken, M. Schäfer, C. Schmitz, G. Homeck, M. Fasdni, Dye-Sensitized Solar Detoxification and Disinfection of Contaminated Water, Proc. 8th Int. Symp. Solar Thermal Concentrating Technologies, Vol. 3, C. F. Müller Verlag, Heidelberg (1997) 1391–1401). However, it is a drawback that large-area covers, as compared to the reaction volume exposed to the radiation, are required which can be manufactured only with a high expenditure, and that a considerable amount of energy has to be applied for repeatedly recirculating the reaction mixture over the falling film surface. Although, in principle, the cover above the falling film could be dispensed with, part of the water and, as the case may be, also low-boiling toxic substances would then evaporate from the falling film surface.

WO 95/06111 relates to a system using tubular photobioreactors for the industrial growth of microorganisms. The bioreactor is arranged essentially horizontal and is positioned between two collectors on different levels.

A similar, comparable arrangement is described in GB 2 118 572 A.

FR 2 685 244 also relates to a device for the growth of microorganisms.

DE 19746 343 A1 relates to a process and device for introducing solar radiation energy into a photoreactor wherein a reactor tube may also be provided in the interior of the reactor.

Recently, the non-light-concentrating multilayer cellular (rib-reinforced) plate reactors, especially double-layer cellular plate reactors, which essentially consist of one or more multilayer cellular plates through which liquid can flow, made of thermoplastically extrudable, transparent or translucent plastics (EP 0 738 686 A1) and CPC (compound parabolic collector) reactors (e.g., J. I. Ajona, A. Vidal, The Use of CPC Collectors For Detoxification Of Contaminated Water: Design, Construction And Preliminary Results, Solar Energy 68 (2000) 109–120) have also been developed and tested for the solar detoxification of contaminated waters. A comparison between reactors showed that both reactor types can altogether be interesting alternatives for solar water purification (R. Dillert, R. Goslich, J. Dzengel, H.-W. Schumacher, D. Bahnemann, Field Studies of Solar Water Detoxification, Proc. 1st Users Workshop Training and Mobility of Researchers Programme at Plataforma Solar de Almería, Nov. 18–19, 1997, Almería, Spain, Ser. Ponencias, Madrid (1998) 31–40). However, it was found that the double-layer cellular plate reactors have a high tendency to fouling and thus exhibit a clearly lower efficiency as compared to CPC reactors. In addition, since the individual reaction channels are bonded together terminally, mechanical cleaning is not possible. In contrast, fouling was not observed with CPC reactors. Another drawback of the multilayer cellular plate reactors is that an integral reactor module must be completely exchanged when one multilayer cellular plate has been damaged. Such a unit has a surface area of, for example, 3.07 $m^2$. The CPC reactors have a drawback in having a complexly shaped reflector structure on the backside. This reflector structure represents a significant cost factor. Depending on the quality of the reflector material, mechanical and/or optical degradation of the mirror structures must also be anticipated in long-term operation.

Line-focusing or point-focusing concentrators have also been used for concentrating the direct radiation from the sun into the reaction apparatus, for example, DE 43 44 163 A1. In the focusing concentrator reactors, the radiation intensity is higher than that of the natural sunlight reaching the earth's surface. This can be advantageous for some applications. However, it is a disadvantage that the focusing apparatus can be operated only when the sky is free of clouds. Therefore, although their operation is attractive in good solar locations, their economically feasible applicability is limited when the weather conditions are less stable. In addition, their installation and operation is associated with a high expenditure. As long as the higher reachable radiation intensity is not required by the process, the increased technical expenditure and costs are critical to their rather not being employed.

For both photochemical and photobiological applications, the costs for providing the light are of considerable importance. With electrically operated light sources, above all, a high capital expense for lamps, power supply and safety measures as well as operating costs for lamp replacement caused by the limited service life of the lamps as well as for cooling and electric power arise.

Systems exclusively operated with sunlight do not exhibit all of these disadvantages. In particular, the high capital expense for lamps and power supply and the operating costs for lamp replacement and electric power do not arise. In addition, for synthetic applications, the expenditure for cooling is significantly lower than for lamp-operated systems. However, there is a major disadvantage as compared to lamp-operated systems in that solar photochemistry and photobiology can be performed only during sunshine periods. However, there is a chance that, in suitable locations, sunlight-operated photochemical or photobiological systems work at lower overall costs than those operated with artificial light.

SUMMARY OF THE INVENTION

A primary object of the invention has been to provide a device and a method which solve the problems known in the prior art, minimize the costs for the solar reactor, consider ease of maintenance and permit sunlight/lamplight hybrid operation.

According to the invention, the above object is achieved in a first embodiment by a device for performing solar photochemical or photobiological reactions, characterized in that the photoreactor consists of one or more transparent outer tubes irradiated with light from the exterior, the reaction medium being passed through the tubes and thereby exposed to the radiation, wherein one or more empty transparent tubes with a smaller diameter are provided in the interior of said outer tubes, especially in a concentric arrangement, and the reaction medium is passed through the gap formed between an outer and an inner tube or, in the case of several inner tubes, through the gaps formed therebetween.

Typically, the transparent tubes are made of glass or a plastic material. In a preferred embodiment, one or more radiation sources, especially tubular radiation sources, are provided in the interior of said inner tubes. Optical waveguide materials or devices by which additional sunlight and/or light from one or more external artificial radiation sources may be introduced into the interior of the reactor, or especially are inserted in the interior of said inner tubes, and preferably, the radiation sources comprise microwave plasma lamps in connection with optical waveguides and diffusers. In another preferred embodiment, the tubes containing the reaction medium are flowed through serially and/or in parallel.

In another embodiment, the invention provides a method for performing solar photochemical or photobiological reactions, characterized in that said reaction is performed in a photoreactor which consists of one or more transparent outer tubes irradiated with light from the exterior and/or simultaneously or alternately also from the interior, the reaction medium being passed through the tubes and thereby exposed to the radiation. Preferably, the photochemical or photobiological reaction is driven by sunlight and/or artificial radiation. Typically, the reactants are passed through the tube containing the reaction medium in a liquid or gaseous phase, neat, homogeneous or heterogeneous, optionally mixed with a solvent or carrier gas. In the method of this invention, the photoreactor may be employed for the photochemical or photobiological storage of the solar energy, or the photoreactor may be employed for the photochemical or photobiological preparation of chemicals. In particular, the photoreactor may be employed for the photonic detoxification and/or disinfection of fluids, especially contaminated water. or the photoreactor may be employed for the photonic detoxification and/or disinfection of contaminated gas streams, especially air.

BRIEF DESCRIPTION OR THE DRAWINGS

DESCRIPTION OF THE EMBODIMENTS

Figure 1:
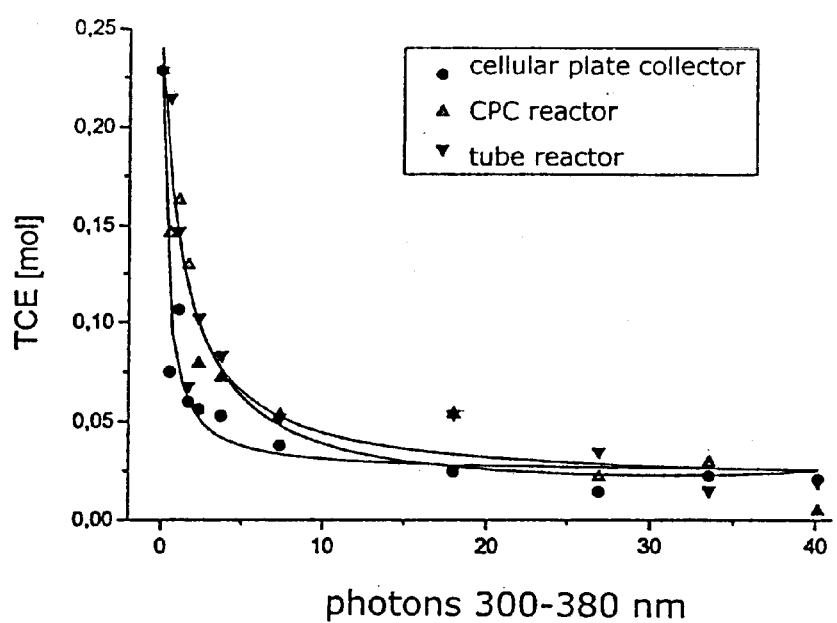
FIG. 1 shows that the same residual concentration of TCE can be reached in all three reactor types with the same quantity of photons.

The key of the approach according to the invention is the making use of the advantages of a solar tube reactor while dispensing with complicated and expensive components. Although sunlight is introduced into a CPC collector reactor more efficiently due to the reflection of the sunlight at the parabolic mirrors provided at the backside as compared to a tube reactor according to this invention, this drawback is compensated for by an enlarged input aperture or extended reaction period. The expenditure for production and mounting is significantly lower than with CPC collector reactors because the compound parabolic mirrors are not required. In addition, the problem of mirror degradation cannot arise. All in all, the additional expenditure for the enlargement of the input aperture for a photoreactor according to this invention is lower than the expenditure for the compound parabolic mirrors.

As compared to multilayer cellular plate reactors, mechanical cleaning operations, if needed, can be easily made after detaching the connecting members between two tube members. If a tube member is damaged, it can be selectively exchanged, which involves lesser costs than for the exchange of a complete reactor module as in the case of multilayer cellular plates.

In one embodiment, an additional tube having a smaller diameter is provided in the reaction tube of the collector, optionally in a concentric arrangement. The medium to be irradiated is passed through the gap between these tubes. For respective reaction systems, the gap width can be easily optimized by methods known to those skilled in the art. For a non-concentrating solar collector reactor, in this embodiment, a high ratio of the quantity of irradiated photons to reaction volume can be achieved without the drawbacks of a falling film reactor. In another embodiment, several empty tubes are provided within the reaction tube, the reaction medium being passed through the gaps therebetween. If one tube is provided, it may be attached in a concentric arrangement, which is not possible for several tubes. However, one tube need not necessarily be provided in a concentric arrangement. Also, for several tubes, the reaction medium is not passed through one gap between two tubes, but through gaps formed between the tubes.

In another particular embodiment, one or more radiation sources, especially lamps, for example, fluorescent tubes or microwave plasma lamps in connection with optical waveguides and diffusers, are provided in the interior of the solar reactor, allowing for hybrid operation. Thus, the operating ability of the device becomes independent of the day-night cycle and of meteorological conditions. Alternatively, it is also possible to use heat sources or cold sources for performing a photochemical or photobiological reaction at a desired temperature. When there is sufficient sunshine, the reactor is irradiated with solar radiation through the exterior tube as in the basic version. When needed, the lamps provide the required radiation. There is an advantage in that no separate capital expense is required for the reactor vessel in the lamp-operated part of the plant, but lamps must only be acquired and positioned in the interior tube or tubes.

In an alternative embodiment, the light supplied by an externally positioned lamp may also be guided into the interior of the reactor by optical waveguide materials. Depending on circumstances, this embodiment may be more easily to service as far as the lamp is concerned. In addition, in this embodiment, additional sunlight may alternatively be guided into the interior of the reactor. Optionally, only part of the reaction tubes may be equipped with lamps. When there is solar irradiation, the introduction of solar radiation and lamplight may also be combined, depending on the process.

EXAMPLES

For comparison with the tube reactor according to the invention, the photocatalytic degradation of the hardly biodegradable model substances trichloroethylene (TCE, $C_2HCl_3$) and oleic acid methyl ester (OME, $C_{19}H_{36}O_2$) was examined in aqueous solution or suspension for illustrative purposes. The other reactor types are a double-layer cellular plate collector supplied by Solacryl, Elsenfeld, Germany, and a CPC reactor supplied by AO SOL, Portugal. During the experiments, all reactors were standing side by side unshaded at the same location in Köln-Porz. All were oriented in an east-west direction with an elevation of 50° with respect to the sun. In addition, all reactors had the same irradiated area (3.07 m$^2$).

FIG. 1 shows that the same residual concentration of TCE can be reached in all three reactor types with the same quantity of photons.

Figure 2:
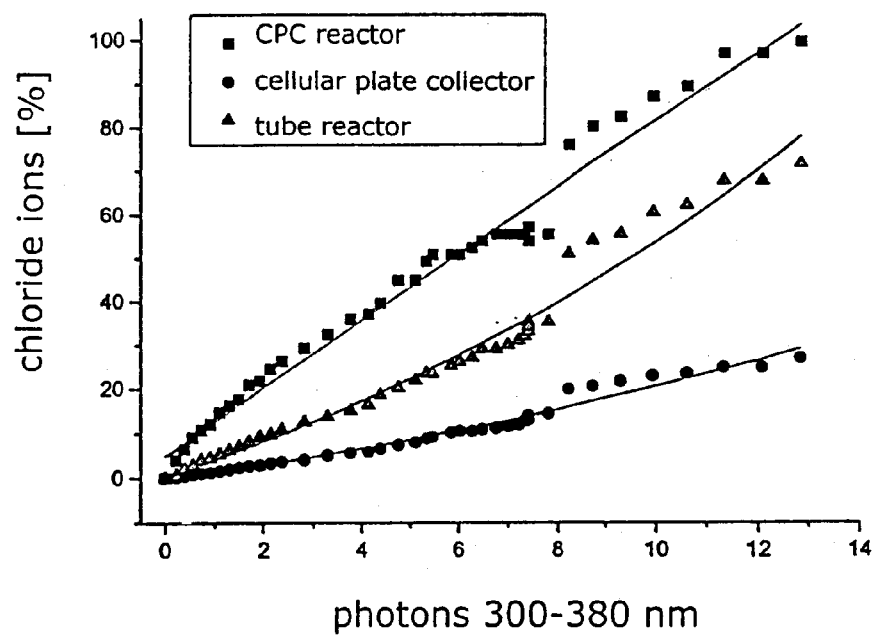
FIG. 2 shows that the mineralization of TCE, as observed by the increase of chloride ion concentration, was most effective in the CPC reactor in these experiments.

FIG. 2 shows that the mineralization of TCE, as observed by the increase of chloride ion concentration, was most effective in the CPC reactor in these experiments. If 100% of the possible amount of chloride ions was formed in the latter, than it is 72% in the tube reactor and only 23% in the cellular plate collector. However, it is to be considered that the constructive and material expenditure for manufacturing the CPC reactor is clearly higher than for the tube reactor. In the tube reactor and in the CPC reactor, the chloride ion formation was very much faster than it was in the double-layer cellular plate collector.

The degradation of OME proceeds even significantly faster and more complete in the tube reactor as compared to the comparative reactors.

Figure 3:
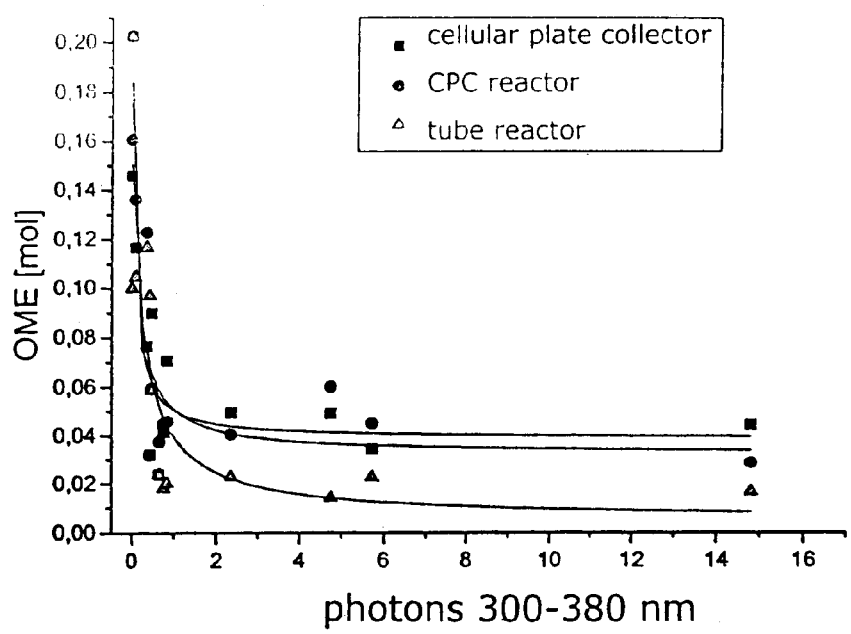
FIG. 3 shows that about 80% of the OME employed was respectively degraded in the double-layer cellular plate collector and in the CPC reactor even after irradiation with 15 mol of photons.

From FIG. 3, it can be seen that about 80% of the OME employed was respectively degraded in the double-layer cellular plate collector and in the CPC reactor even after irradiation with 15 mol of photons. In contrast, in the tube reactor, as much as 90% of the OME is degraded already with 2 mol of photons, and more than 95% with 10 mol of photons.

Figure 4:
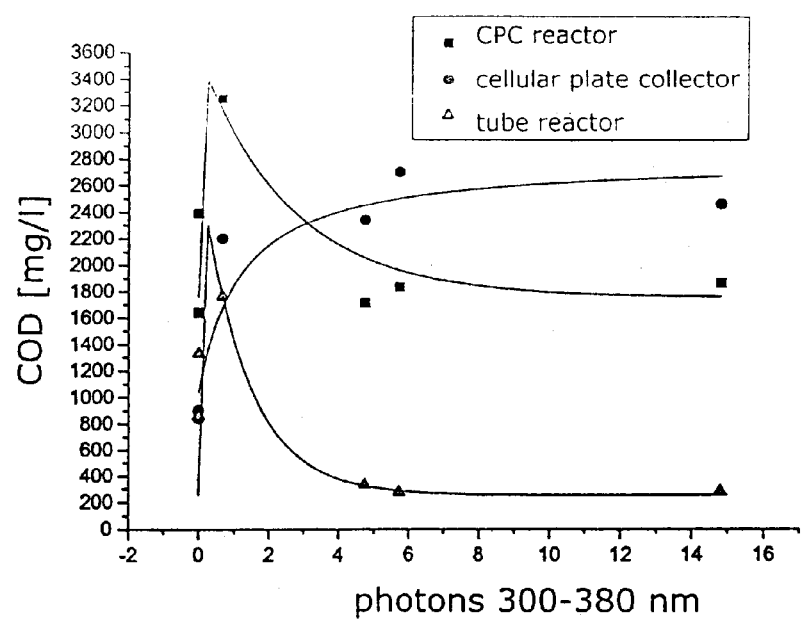
FIG. 4 shows the result of the same experiment when chemical oxygen demand (COD) is the measured quantity.

This result is even more clearly shown when the chemical oxygen demand (COD) is considered the measured quantity in FIG. 4.

In all three reactors, the same degradation experiment was performed with 1000 mg/l OME. In the cellular plate collector, the COD increases relatively slowly and remains constant on a high level of about 70% of its theoretical value. A further degradation of the organic molecules does not occur. In the CPC reactor, the COD increases very rapidly to a maximum value and then decreases in accordance with the experiments using TCE. However, in this case too, the degradation comes to a halt at a COD of 50% of the theoretically possible value. In the tube reactor, a similar degradation is observed as in the CPC reactor, but with the degradation being almost complete.

What is claimed is:

1. A photoreactor device for performing solar photochemical or photobiological reactions, characterized in that the photoreactor consists essentially of (1) one or more transparent outer tubes irradiated with light from the exterior, a reaction medium being passed through the tubes and thereby exposed to the radiation, and (2) one or more empty transparent tubes with a smaller diameter provided in the interior of said outer tubes, wherein the reaction medium is passed through the gap formed between an outer and an inner tube or, in the case of several inner tubes, through the gap formed therebetween.

2. The device according to claim 1, wherein said tubes with smaller diameter are concentric with said outer tubes.

3. The device according to claim 1, characterized in that said transparent tubes are made of glass or a plastic material.

4. The device according to any one of claims 1–3, characterized in that one or more radiation sources are provided in the interior of said inner tubes.

5. The device according to claim 4, wherein said radiation sources are tubular radiation sources.

6. The device according to any one of claims 1–3, characterized in that optical waveguide materials or devices by which additional sunlight, light from one or more external artificial radiation sources, or a combination thereof, is introduced into the interior of the reactor.

7. The device according to claim 6, wherein optical waveguide materials or said devices are inserted in the interior of said inner tubes.

8. The device according to claim 6, characterized in that said radiation sources comprise microwave plasma lamps in connection with optical waveguides and diffusers.

9. The device according to any one of claims 1–3, characterized in that the reaction medium flows through said tubes serially or in parallel or a combination thereof.

10. A method for performing solar photochemical or photobiological reactions, characterized in that said reaction is performed in a photoreactor consisting essentially of (1) one or more transparent outer tubes irradiated with light from the exterior of said tubes, a reaction medium being passed through the tubes and thereby exposed to the radiation, and (2) one or more empty transparent tubes with a smaller diameter are provided in the interior of said outer tubes, wherein the reaction medium is passed through the gap formed between an outer and an inner tube or, in the case of several inner tubes, through the gap formed therebetween.

11. The method according to claim 10, characterized in that the reactants are passed through the tube containing the reaction medium in a liquid or gaseous phase, neat, homogeneous or heterogenous, optionally mixed with a solvent or carrier gas.

12. The method according to claim 10 or 11, characterized in that said photochemical or photobiological reaction is driven by sunlight, artificial radiation or a combination thereof.

13. The method according to claim 12, characterized in that said photoreactor is employed for the photochemical or photobiological storage of the solar energy.

14. The method according to any one of claim 10 or 11, characterized in that said photoreactor is employed for the photochemical or photobiological preparation of chemicals.

15. The method according to any one of claim 10 or 11, characterized in that said photoreactor is employed for the photonic detoxification and/or disinfection of fluids.

16. The method according to claim 15, wherein the fluid is contaminated water.

17. The method according to any one of claim 10 or 11, characterized in that said photoreactor is employed for the photonic detoxification and/or disinfection of contaminated gas streams.

18. The method according to claim 17, wherein the gas stream is air.

* * * * *